(12) United States Patent
Sato et al.

(10) Patent No.: US 7,618,914 B2
(45) Date of Patent: Nov. 17, 2009

(54) METHOD FOR PRODUCING HYDROXYLAMINE COMPOUND USING PLATINUM CATALYST FIXED ON ION-EXCHANGE RESIN

(75) Inventors: Mutsumi Sato, Saitama (JP); Keiji Oono, Saitama (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 528 days.

(21) Appl. No.: 10/545,073

(22) PCT Filed: Jan. 22, 2004

(86) PCT No.: PCT/JP2004/000529

§ 371 (c)(1),
(2), (4) Date: Aug. 9, 2005

(87) PCT Pub. No.: WO2004/072019

PCT Pub. Date: Aug. 26, 2004

(65) Prior Publication Data

US 2006/0106254 A1  May 18, 2006

(30) Foreign Application Priority Data

Feb. 14, 2003  (JP) .............................. 2003-036769

(51) Int. Cl.
*B01J 31/00* (2006.01)
*B01J 27/185* (2006.01)

(52) U.S. Cl. .................. 502/159; 502/150; 502/213

(58) Field of Classification Search ................ 502/159, 502/150, 213; 564/300
See application file for complete search history.

(56) References Cited

U.S. PATENT DOCUMENTS

| | | | | |
|---|---|---|---|---|
| 3,694,509 A | * | 9/1972 | Rylander et al. | |
| 4,621,149 A | * | 11/1986 | Fukuoka et al. | ................ 560/24 |
| 4,723,030 A | * | 2/1988 | Davis | |
| 5,166,435 A | * | 11/1992 | Sharma et al. | ............... 564/300 |
| 5,648,307 A | * | 7/1997 | Yasuda et al. | ................ 502/101 |
| 5,739,134 A | * | 4/1998 | Van Daele et al. | ........... 514/249 |
| 6,031,106 A | * | 2/2000 | Harreus et al. | ............... 546/334 |
| 2002/0107273 A1 | * | 8/2002 | Nakao et al. | ................. 514/394 |
| 2003/0139629 A1 | * | 7/2003 | Vandersall et al. | |

FOREIGN PATENT DOCUMENTS

| | | | | |
|---|---|---|---|---|
| EP | 0 086 363 A1 | * | 8/1983 | |
| JP | 58-164549 | * | 9/1983 | |
| JP | 62-63548 | * | 3/1987 | |
| JP | 10-59707 | * | 3/1998 | |
| JP | 2003-62468 | * | 3/2003 | |
| JP | 2003-212812 | * | 7/2003 | |

* cited by examiner

*Primary Examiner*—Michael A Marcheschi
*Assistant Examiner*—James E McDonough
(74) *Attorney, Agent, or Firm*—Edwards Angell Palmer & Dodge LLP

(57) ABSTRACT

The present invention discloses a method for producing a hydroxylamine compound wherein a nitro compound is contacted with a hydrogen source or further with a poisoning agent in the presence of a platinum catalyst fixed on an ion-exchange resin. According to the method of the present invention where a platinum catalyst fixed on a matrix of an ion-exchange resin is used, the objective hydroxylamine compound can be produced (manufactured) efficiently, more industrially and safely with little formation of a byproduct. Further, the platinum catalyst fixed on an ion-exchange resin of the present invention is hardly deactivated even if repeatedly used many times because platinum metal is fixed on a matrix of the ion-exchange resin, and handling in recovery, reuse and the like of said catalyst is extremely easy because particle size of said catalyst is very large.

14 Claims, No Drawings

METHOD FOR PRODUCING HYDROXYLAMINE COMPOUND USING PLATINUM CATALYST FIXED ON ION-EXCHANGE RESIN

TECHNICAL FIELD

The present invention relates to a method for producing a hydroxylamine compound from a nitro compound using a platinum catalyst fixed on an ion-exchange resin.

BACKGROUND

Hydroxylamine compounds are very important compounds as intermediate products for, for example, polymerization inhibitors, antioxidants, agricultural chemicals, medicines, cosmetics and electronic industrial chemicals.

Phenylhydroxylamine as an example of the hydroxylamine compound is a useful compound as an intermediate product for polymerization inhibitors and antioxidants, and had been conventionally manufactured by a method where nitrobenzene is reduced with sodium hydrosulfide or a method where nitrobenzene is reacted with hydrogen using a platinum-carbon catalyst (see, U.S. Pat. No. 3,694,509).

However, in the former method, yield of an objective product is not high enough to be practically used due to a low selectivity of the reaction, and there is fear that offensive odor of sodium hydrosulfide to be used affect working environment.

On the other hand, in the latter method, yield of an objective product is not high enough to be commercially used similarly to the former method, and there is a problem that elevation of reaction temperature to improve the yield results in, on the contrary, lowering of the yield due to decrease of reaction selectivity. Further, in the latter method, not only formation ratio of aniline as a byproduct is high but also platinum-carbon to be used as a reaction catalyst requires special attention in handling because of a combustible substance. Still further, recovery and reuse of the above platinum catalyst after use requires extremely complicated procedures due to a very small particle size.

Under the above circumstances, development of a method for manufacturing (producing) a hydroxylamine compound efficiently, industrially and safely is demanded.

DISCLOSURE OF THE INVENTION

The present invention provides a method for producing a hydroxylamine compound, wherein a nitro compound is contacted with a hydrogen source in the presence of a platinum catalyst fixed (immobilized) on an ion-exchange resin.

That is, the present inventors, after extensively studied to solve the above problems, have found that the objective hydroxylamine compound can be obtained efficiently, industrially and safely by using a catalyst where a platinum metal is fixed (supported) on a matrix of an ion-exchange resin, namely, a platinum catalyst fixed on an ion-exchange resin, and the catalyst fixed on the ion-exchange resin is not only easy to handle but also easy to recover and reuse due to a large particle size thereof, and completed the present invention.

BEST MODE FOR CARRYING OUT THE INVENTION

A platinum catalyst fixed on an ion-exchange resin of the present invention is one that can be obtained by adsorbing a platinum-containing ion in an aqueous solvent with a suitable ion-exchange resin followed by subjecting the ion to a reductive treatment. In said catalyst, the platinum metal is fixed on a matrix of the ion-exchange resin. Here, the platinum-containing ion means an anion or a cation derived from a platinum compound or a platinum complex which contains, for example, 1- to 6-valent, more specifically bivalent, tetravalent and hexavalent platinum ions or platinum atom.

When the platinum catalyst fixed on an ion-exchange resin of the present invention is obtained, a platinum compound to be dissolved in the aqueous solvent in order to make the platinum-containing ion present in the aqueous solvent includes, for example, platinum metal, platinum oxides such as $PtO_2$; platinum halides such as platinum chloride, platinum bromide and platinum iodide; ammonium platinates such as ammonium hexachloroplatinate and ammonium tetrachloroplatinate; potassium halogenated platinates such as potassium hexachloroplatinate, potassium tetrachloroplatinate and potassium tetrabromoplatinate; sodium halogenated platinates such as sodium hexachloroplatinate and sodium tetrachloroplatinate; platinum nitrate; platinum sulfate; platinum acetate; and platinum complexes coordinated with a ligand. Among others, potassium halogenated platinates and sodium halogenated platinates are preferable, and potassium tetrachloroplatinate and sodium tetrachloroplatinate are particularly preferable.

The ligand of the platinum complexes coordinated with a ligand includes, for example, 1,5-cyclooctadiene (COD), dibenzylideneacetone (DBA), norbornadiene (NBD), tricyclohexylphosphine ($PCy_3$), triethoxyphosphine ($P(OEt)_3$), tri-tert-butylphosphine ($P(O^tBu)_3$), bipyridine (BPY), phenanthroline (PHE), triphenylphosphine ($PPh_3$), 1,2-bis(diphenylphosphino)ethane (DPPE), triphenoxyphosphine ($P(OPh)_3$), trimethoxyphosphine ($P(OCH_3)_3$), ethylene ($CH_2\!\!=\!\!CH_2$), amine($NH_3$), $N_2$ and $PO_3$.

When the platinum catalyst fixed on an ion-exchange resin of the present invention is obtained, the ion-exchange resin to be used includes one consisting of a so-called skeletal polymer to which an ion-exchange group bonded. Said skeletal polymer includes, for example, one obtained by polymerizing or copolymerizing a monomer represented by the following general formula [1]:

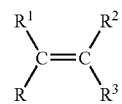

[1]

(wherein, R and $R^1$ represent each independently a hydrogen atom, a lower alkyl group, a carboxyl group, a carboxyalkyl group, an alkyloxycarbonyl group, a hydroxyalkyloxycarbonyl group, a cyano group or a formyl group; $R^2$ represents a hydrogen atom, a lower alkyl group, a carboxyl group, an alkyloxycarbonyl group, a hydroxyalkyloxycarbonyl group, a cyano group or a halogen atom; $R^3$ represents a hydrogen atom, a lower alkyl group, a haloalkyl group, a hydroxyl group, an aryl group which may have a substituent, an aliphatic heterocyclic group, an aromatic heterocyclic group, a halogen atom, an alkyloxycarbonyl group, a hydroxyalkyloxycarbonyl group, a sulfo group, a cyano group, a cyano-containing alkyl group, an acyloxy group, a carboxyl group, a carboxyalkyl group, an aldehyde group, an amino group, an aminoalkyl group, a carbamoyl group, a N-alkylcarbamoyl group or a hydroxyalkyl group; and R and $R^4$ or $R^1$ and $R^2$ may form an aliphatic ring together with the adjacent —C=C— bond).

The lower alkyl group represented by R and $R^1$ to $R^3$ in the general formula [1] may be straight chained, branched or cyclic, and includes, for example, an alkyl group having 1 to 6 carbon atoms, and is specifically exemplified by a methyl group, an ethyl group, a n-propyl group, an isopropyl group, a n-butyl group, an isobutyl group, a tert-butyl group, a sec-butyl group, a n-pentyl group, an iso-pentyl group, a tert-pentyl group, a 1-methylpentyl group, a n-hexyl group, an iso-hexyl group, a cyclopropyl group, a cyclopentyl group and a cyclohexyl group.

The carboxyalkyl group represented by R, $R^1$ and $R^2$ includes, for example, one where a part of hydrogen atoms of the above-described lower alkyl group is replaced by a carboxyl group, and is specifically exemplified by, for example, a carboxymethyl group, a carboxyethyl group, a carboxypropyl group, a carboxybutyl group, a carboxypentyl group and a carboxyhexyl group.

The alkyloxycarbonyl group represented by R and $R^1$ to $R^3$ preferably includes, for example, one having 2 to 11 carbon atoms, and is specifically exemplified by, for example, a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, a 2-ethylhexyloxycarbonyl group, a octyloxycarbonyl group, a nonyloxycarbonyl group and a decyloxycarbonyl group.

The hydroxyalkyloxycarbonyl group represented by R and $R^1$ to $R^3$ includes one where a part of hydrogen atoms of the above-described alkyloxycarbonyl group is replaced by a hydroxyl group, and is specifically exemplified by, for example, a hydroxymethyloxycarbonyl group, a hydroxyethyloxycarbonyl group, a hydroxypropyloxycarbonyl group, a hydroxybutyloxycarbonyl group, a hydroxypentyloxycarbonyl group, a hydroxyhexyloxycarbonyl group, a hydroxyheptyloxycarbonyl group, a hydroxyoctyloxycarbonyl group, a hydroxynonyloxycarbonyl group and a hydroxydecyloxycarbonyl group.

The halogen atom represented by $R^2$ and $R^3$ includes, for example, fluorine, chlorine, bromine and iodine.

The haloalkyl group represented by $R^3$ includes, for example, the above-described lower alkyl group having 1 to 6 carbon atoms represented by $R^1$ to $R^3$ which is halogenated (for example, fluorinated, chlorinated, brominated and iodinated), and is specifically exemplified by, for example, a chloromethyl group, a bromomethyl group, a trifluoromethyl group, a 2-chloroethyl group, a 3-chloropropyl group, a 3-bromopropyl group, a 3,3,3-trifluoropropyl group, a 4-chlorobutyl group, a 5-chloropentyl group and a 6-chlorohexyl group.

The aryl group of the aryl group which may have a substituent includes, for example, a phenyl group, a tolyl group, a xylyl group and a naphthyl group, and said substiutent includes, for example, an amino group, a hydroxyl group, a lower alkoxy group and a carboxyl group. Specific examples of the substituted aryl group include, for example, an aminophenyl group, a toluidino group, a hydroxyphenyl group, a methoxyphenyl group, a tert-butoxyphenyl group and a carboxyphenyl group.

The aliphatic heterocyclic group preferably includes, for example, 5-membered or 6-membered one containing 1 to 3 hetero atoms such as a nitrogen atom, an oxygen atom and a sulfur atom, and is exemplified by, for example, a pyrolidil-2-on group, a pyperidyl group, a pyperidino group, a pyperadinyl group and a morpholino group.

The aromatic heterocyclic group preferably includes, for example, 5-membered or 6-membered one containing 1 to 3 hetero atoms such as a nitrogen atom, an oxygen atom and a sulfur atom, and is exemplified by, for example, a pyridil group, an imidazolyl group, a thiazolyl group, a furanyl group and a piranyl group.

The cyano-containing alkyl group includes, for example, one where a part of hydrogen atoms of the above-described lower alkyl group is replaced by a cyano group, and is exemplified by, for example, a cyanomethyl group, a 2-cyanoethyl group, a 2-cyanopropyl group, a 3-cyanopropyl group, a 2-cyanobutyl group, a 4-cyanobutyl group, a 5-cyanopentyl group and a 6-cyanohexyl group.

The acyloxy group includes, for example, one derived from a carboxylic acid having 2 to 20 carbon atoms, and is specifically exemplified by, for example, an acetyloxy group, a propionyloxy group, a butylyloxy group, a pentanoyloxy group, a nonanoyloxy group, a decanoyloxy group and a benzoyloxy group.

The aminoalkyl group includes one where a part of hydrogen atoms of the above-described lower alkyl group is replaced by an amino group, and is specifically exemplified by, for example, an aminomethyl group, an aminoethyl group, an aminopropyl group, an aminobutyl group, an amonopentyl group and an aminohexyl group.

The N-alkylcarbamoyl group includes one where a part of hydrogen atoms of the carbamoyl group is replaced by an alkyl group, and is specifically exemplified by, for example, a N-methylcarbamoyl group, a N-ethylcarbamoyl group, a N-n-propylcarbamoyl group, a N-isopropylcarbamoyl group, a N-n-butylcarbamoyl group and a N-t-butylcarbamoyl group.

The hydroxylalkyl group includes one where a part of hydrogen atoms of the above-described lower alkyl group is replaced by a hydroxyl group, and is specifically exemplified by, for example, a hydroxymethyl group, a hydroxyethyl group, a hydroxypropyl group, a hydroxybutyl group, a hydroxypentyl group and a hydroxyhexyl group.

The aliphatic ring when R and $R^2$ or $R^1$ and $R^2$ form an aliphatic ring together with the adjacent —C=C— bond includes, for example, an unsaturated aliphatic ring having 5 to 10 carbon atoms, and the ring may be monocyclic or polycyclic. Specific examples of these rings include, for example, a norbornene ring, a cyclopeantene ring, a cyclohexene ring, a cyclooctene ring and a cyclodecene ring.

Specific examples of the monomer represented by the general formula [1] include, for example, ethylenically unsaturated aliphatic hydrocarbons having 2 to 20 carbon atoms such as ethylene, propylene, butylene and isobutylene; ethylenically unsaturated aromatic hydrocarbons having 8 to 20 carbon atoms such as styrene, 4-methylstyrene, 4-ethylstyrene and divinylbenzene; alkenyl esters having 3 to 20 carbon atoms such as vinyl formate, vinyl acetate, vinyl propionate, isopropenyl acetate; halogen-containing ethylenically unsaturated compounds having 2 to 20 carbon atoms such as vinyl chloride, vinylidene chloride, vinylidene fluoride and tetrafluoroethylene; ethylenically unsaturated carboxylic acids having 3 to 20 carbon atoms such as acrylic acid, methacrylic acid, itaconic acid, maleic acid, fumaric acid, crotonic acid, vinylacetic acid, allylacetic acid and vinylbenzoic acid (these acids may be in a form of salt with an ammonium or an alkali metal such as sodium and potassium) ethylenically unsaturated carboxylic acid esters such as methyl methacrylate, ethyl methacrylate, propyl methacrylate, butyl methacrylate, 2-ethylhexyl methacrylate, methyl acrylate, ethyl acrylate, propyl acrylate, butyl acrylate, 2-ethylhexyl acrylate, lauryl methacrylate, stearyl acrylate, methyl itaconate, ethyl itaconate, methyl maleate, ethyl maleate, methyl fumarate, ethyl fumarate, methyl crotonate, ethyl crotonate and methyl 3-butenate; cyan-containing ethylenically unsaturated compounds having 3 to 20 carbon atoms such as acrylonitrile, methacrylonitrile and allyl cyanide; ethylenically unsaturated amid compounds having 3 to 20 carbon atoms such as acrylamide and methacrylamide; ethylenically unsaturated aldehydes having 3 to 20 carbon atoms such as acrolein and crotonaldehyde; ethylenically unsaturated sulfonic acids having 2 to 20 carbon atoms such as vinylsulfonic acid and 4-vinylbenzenesulfonic acid (these acids may form an salt such as alkali metal salt with sodium or potassium); ethylenically unsaturated aliphatic amines having 2 to 20 carbon atoms such as vinylamine and allylamine; etylenically unsaturated aromatic amines having 8 to 20 carbon atoms such as vinylaniline; ethylenically unsaturated aliphatic heterocyclic amines having 5 to 20 carbon atoms such as N-vinylpyrolidone and vinylpiperidine; ethylenically unsaturated alcohols having 3 to 20 carbon atoms such as allylalcohol and crotylalcohol; and ethylenically unsaturated phenols having 8 to 20 carbon atoms such as 4-vinylphenol.

The above-described skeletal polymer constructing the platinum catalyst fixed on an ion-exchange resin preferably includes, for example, a copolymer of styrene based resin or acrylic ester based resin cross-linked with a bifunctional monomer such as divinlbenzene, butadiene, isoprene, vinyl acrylate, vinyl methacrylate, allyl acrylate, allyl methacrylate, ethylene diacrylate, ethylene dimethacrylate, 1,4-butanediol acrylate, 1,6-hexanediol acrylate, ethyleneglycol dimethacrylate, 1,3-butanediol dimethacryalte, triethyleneglycol dimethacrylate and N,N-methylene-bis(acrylamide), and specifically exemplified by, for example, a styrene-divinylbenzene copolymer and a methyl acrylate-divinylbenzene copolymer.

The ion-exchange group bonded to the above-described skeletal polymer to form an ion-exchange resin includes, for example, a cation exchange group and an anion exchange group, and preferably an anion exchange group in the method of the present invention.

The above anion-exchange group includes, for example, a weak basic anion-exchange group and a strong basic anion-exchange group, and the cation-exchange group includes, for example, a weak acidic cation-exchange group and a strong acidic cation-exchange group.

Basic property of the anion-exchange resin is determined by basic property of the basic group constructing the anion-exchange group bonded to said anion-exchange resin. If said basic group is a weak basic group, the resin has weak basic property, and if the basic group is a strong basic group, the resin has strong basic property. That is, basic property of the anion-exchange resin itself can be adjusted by properly varying basic property of the basic group.

Further, acidic property of the cation-exchange resin is determined by acidic property of the acidic group constructing the cation-exchange group bonded to said cation-exchange resin. If said acidic group is a weak acidic group, the resin has weak acidic property, and if the acidic group is a strong acidic group, the resin has strong acidic property. That is, acidic property of the cation-exchange resin itself can be adjusted by properly varying acidic property of the acidic group.

The anion-exchange group constructing the above-described ion-exchange resin includes, for example, basic groups of amino groups such as a primary amino group, a secondary amino group, a tertiary amino group and a quaternary amino group and diamines such as alkyldiamine. Among others, a tertiary amino group and a quaternary ammonium group are preferable, and a quaternary ammonium group is particularly preferable.

In the above-described basic groups, for example, a primary amino group, a secondary amino group, a tertiary amino group and diamines are weak basic anion-exchange groups, and for example, a quaternary ammonium group is strong basic anion-exchange group.

In the anion-exchange group, the secondary amino group includes, for example, one represented by the general formula [2]:

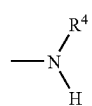

[2]

(wherein, $R^4$ represents an alkyl group, an aryl group, an aralkyl group or a hydroxyalkyl group), and the tertiary amino group includes, for example, one represented by the following general formula [3]:

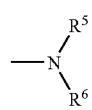

[3]

(wherein, $R^5$ and $R^6$ represent each independently an alkyl group, an aryl group, an aralkyl group or a hydroxyalkyl group), and further the quaternary ammonium group includes, for example, one represented by the following general formula [4]:

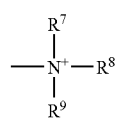

[4]

(wherein, $R^7$, $R^8$ and $R^9$ represent each independently an alkyl group, an aryl group, an aralkyl group or a hydroxyalkyl group).

In the above-described general formulas [2], [3] and [4], the alkyl group represented by $R^4$ to $R^9$ may be straight chained, branched or cyclic, and has generally 1 to 10 carbon atoms, preferably 1 to 6 carbon atoms, more preferably 1 to 4 carbon atoms, further more preferably 1 or 2 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a 3-methylpentyl group, a 2-methylpentyl group, a 1,2-dimethylbutyl group, a n-heptyl group, a n-isoheptyl group, a sec-heptyl group, a n-octyl group, an isooctyl group, a sec-octyl group, a n-nonyl group, a n-decyl group, a cyclopropyl group, a cyclobutyl group, a cyclopentyl group, a cyclohexyl group, a cycloheptyl group, a cyclooctyl group, a cyclononyl group and a cyclodecyl group.

In the general formulas [2], [3] and [4], the aryl group represented by $R^4$ to $R^9$ includes one having generally 6 to 10 carbon atoms and preferably 6 carbon atoms, which is specifically exemplified by, for example, a phenyl group and a naphtyl group. These aryl groups may have generally 1 to 5, preferably 1 to 2 substituents such as an alkyl group and a hydroxyl group.

The alkyl group of the above-described aryl group which may have an alkyl group may be straight chained, branched or cyclic, and includes one having generally 1 to 4 carbon atoms, preferably 1 to 2 carbon atoms, which is specifically exemplified by, for example, a methyl group, an ethyl group, a n-propyl group, an isopropyl group, a n-butyl group, an isobutyl group, a sec-butyl group, a tert-butyl group, a cyclopropyl group and a cyclobutyl group.

In the general formulas [2], [3] and [4], the aralkyl group represented by $R^4$ to $R^9$ includes one having generally 7 to 10 carbon atoms, which is specifically exemplified by, for example, a benzyl group, a phenylethyl group, a phenylpropyl group and a phenylbutyl group.

In the general formulas [2], [3] and [4], the hydroxyalkyl group represented by $R^4$ to $R^9$ includes, for example, one where one of hydrogen atoms of the above-described alkyl group represented by $R^4$ to $R^9$ is replaced by a hydroxyl group, which is specifically exemplified by, for example, a hydroxylmethyl group, a hydroxyethyl group, a hydroxypropyl group, a hydroxybutyl group, a hydroxypentyl group, a hydroxyhexyl group, a hydroxyheptyl group, a hydroxyoctyl group, a hydroxynonyl group, a hydroxydecyl group, a hydroxycyclopropyl group, a hydroxycyclobutyl group, a hydroxycyclopentyl group, a hydroxycyclohexyl group, a hydroxycycloheptyl group, a hydroxycyclooctyl group, a hydroxycyclononyl group and a hydroxycyclodecyl group. Among others, a hydroxymethyl group and a hydroxyethyl group are preferable, and a hydroxyethyl group is particularly preferable.

Particularly preferable specific examples of the tertiary amino group represented by the above-described general formula [3] include the following groups:

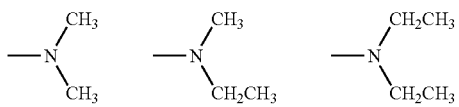

and particularly preferable specific examples of the quaternary ammonium group represented by the above-described general formula [4] include the following groups:

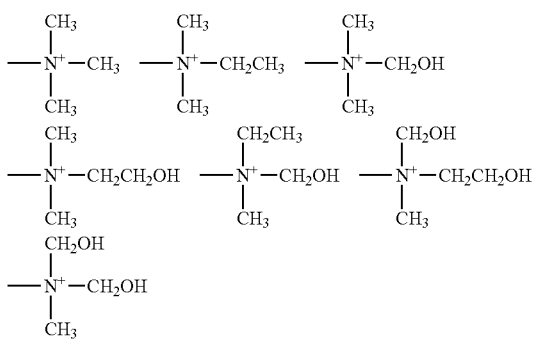

The above-described quaternary ammonium group is provided generally in an ionically bonded state with a suitable anion. The anion which is ionically bonded to the quaternary ammonium group includes, for example, halogen ions such as a chloride ion, a bromide ion, a fluoride ion and an iodide ion, a hydroxide ion, a sulfate ion and an acetate ion. Among others, a chloride ion is preferable.

Further, the alkyldiamine group as the anion-exchange group includes a group represented by the following general formula [5]:

$$—NH—A—NH_2 \qquad [5]$$

(wherein, A represents an alkylene group).

In the general formula [5], the alkylene group represented by A may be straight chained, branched or cyclic, preferably straight chained, having generally 1 to 10 carbon atoms, preferably 1 to 6 carbon atoms, more preferably 1 to 4 carbon atoms and further more preferably 2 carbon atoms, which is specifically exemplified by, for example, a methylene group, an ethylene group, a trimethylene group, a propylene group, a methylmethylene group, a methylethylene group, an ethylmethylene group, a tetramethylene group, an ethylethylene group, a propylmethylene group, a pentamethylene group, a hexamethylene group, a heptamethylene group, an octamethylene group, a nonamethylene group, a decamethylene group, a cyclopropylene group, a cyclobutylene group, a cyclopentylene group, a cyclohexylene group, a cycloheptylene group, a cyclooctylene group, a cyclononylene group and a cyclodecylene group.

Particularly preferable specific examples of the alkyldiamine group represented by the above-described general formula [5] include, for example, the following groups:

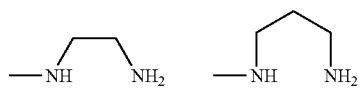

Further, the cation-exchange group constructing the above-described ion-exchange resin includes, for example, a sulfonic acid group and a carboxyl group. Among others, a sulfonic acid group is preferable.

In the above-described cation-exchange groups, for example, sulfonic acid group belongs to the strong acid cation-exchange groups, and, for example, a carboxyl group and a phenolic hydroxyl group belong to the weak acid cation-exchange groups.

The most preferable specific examples of the ion-exchange group of the ion-exchange resin used in the method of the present invention include the following anion-exchange groups:

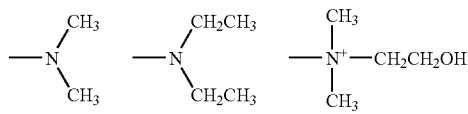

Preferable specific examples of the ion-exchange resin used in the method of the present invention include, for example, an anion-exchange resin consisting of a polystyrene copolymer cross-linked with divinylbenzene which has the above-described anion-exchange group such as a tertiary amino group or a quaternary ammonium group bonded to an aromatic ring thereof, and a polyacrylic ester which has the above-described anion-exchange group such as a tertiary amino group or a quaternary ammonium group bonded to a carbonyl moiety of an ester group thereof, and a cation-exchange resin consisting of a polystyrene copolymer cross-linked with divinylbenzene which has the above-described cation-exchange group such as a sulfonic acid group or a carboxyl group bonded to an aromatic ring thereof and a polyacrylic ester which has the above-described cation-exchange group such as a sulfonic acid group or a carboxyl group bonded to a carbonyl moiety of an ester group thereof.

The anion-exchange resin or the cation-exchange resin used in the method of the present invention may be one which is synthesized by the known technique or one on the market. Typical examples of the anion-exchange resin on the market include, for example, DOWEX (Trade Name, made by Dow Chemical Co.), DUOLITE (Trade Name, made by Diamond Shamrock Corp.), AMBERLITE (Trade Name, made by Rohn & Haas Co.), NALCITE (Trade Name, made by Nalco Chemical Co.), IRA-410JC1 (Trade Name, made by Organo Corp.), and IRA-400JC1 (Trade Name, made by Organo Corp.), and typical examples of the cation-exchange resin include, for example, IR-120B Na (Trade Name, made by Organo Corp.).

As described above, the platinum catalyst fixed on an ion-exchange resin of the present invention can be easily prepared by adsorbing the platinum-containing ion, which is obtained by dissolving a platinum compound in an aqueous solvent, on an ion-exchange resin as a carrier, followed by subjecting to a reductive treatment.

The aqueous solvent used for dissolving a platinum compound to obtain the platinum catalyst fixed on an ion-exchange resin includes, for example, alcohols having generally 1 to 4 carbon atoms such as methanol, ethanol, propanol and butanol; ketones such as acetone and methylethylketone; esters such as ethyl acetate and butyl acetate; aqueous organic solvents such as acetonitrile and dimethylformamide, or a mixture thereof. Among others, a water-containing solvent is preferable and water only is particularly preferable. Said aqueous solvent may be properly added with an acid such as hydrochloric acid, sulfuric acid and nitric acid or a base such as sodium hydroxide and potassium hydroxide to make the dissolution of a platinum compound easy.

Since all types of the platinum catalyst fixed on an ion-exchange resin of the present invention are similarly black colored in appearance irrespective of a type of platinum compound used for preparation thereof, it is presumed that the platinum metal itself is fixed (immobilized or supported) on a matrix of an ion-exchange resin.

Amount of the platinum compound to be used for preparing the platinum catalyst fixed on an ion-exchange resin of the present invention is an amount so that a ratio of the weight of Pt to the total weight of the platinum catalyst fixed on an ion-exchange resin becomes generally 0.0001 to 50% by weight, preferably 0.01 to 20% by weight, and more preferably 0.01 to 10% by weight.

Herein below, the method for preparing the platinum catalyst fixed on an ion-exchange resin will be described more specifically using a case where an anion-exchange resin is used as an example.

For example, a platinum compound which can release a platinum-containing anion such as $K_2PtCl_4$ is dissolved in an aqueous solvent containing a mineral acid such as hydrochloric acid and sulfuric acid if necessary, followed by mixing said solution and an anion-exchange resin, then leaving for standing if necessary. Then, the precipitates are filtered, washed and dried, followed by subjecting it to a reductive treatment using a suitable reducing agent such as hydrogen gas and hydrazine to obtain the platinum catalyst fixed on an anion-exchange resin of the present invention where the platinum metal is fixed on a matrix of an anion-exchange resin.

Further, herein below, the method for preparing the platinum catalyst fixed on an ion-exchange resin will be described more specifically using another case where a cation-exchange resin is used as an example.

For example, a platinum compound which can release a platinum-containing cation such as $[H_2NCH_2CH_2NH_2]Pt](NO_3)_2$ is dissolved in an ion-exchanged water, followed by mixing said solution and a cation-exchange resin, then leaving for standing if necessary. Then, the precipitates are filtered, washed and dried, followed by subjecting it to a reductive treatment using a suitable reducing agent such as hydrogen gas and hydrazine to obtain the platinum catalyst fixed on a cation-exchange resin of the present invention where the platinum metal is fixed on a matrix of a cation-exchange resin.

The above-described reducing agent used for manufacturing the platinum catalyst fixed on an ion-exchange resin may be a compound generally used as a reducing compound. Among others, preferable specific examples include, for example, hydrogen gas, hydrazine, sodium hydroborate, ammonium formate, diethylammonium formate, sodium hypophosphite, potassium hypophosphite, carbon monoxide and ethylene.

Temperature of the reductive treatment is generally −20 to 200° C., preferably 0 to 100° C., and more preferably 10 to 60° C., and the reductive treatment may be carried out in accordance with the known method.

The objective hydroxylamine compound can be obtained by contacting a nitro compound with a hydrogen source in the presence of the thus obtained platinum catalyst fixed on an ion-exchange resin.

In the method of the present invention, the nitro compound includes, for example, a compound represented by the general formula [6]:

$$R^{10}\text{—}NO_2 \qquad [6]$$

(wherein, $R^{10}$ represents an alkyl group, an aryl group or an aralkyl group which may contain a hydrogen atom or a hetero atom and also have a substituent).

In the general formula [6], the alkyl group represented by $R^{10}$ may be straight chained, branched or cyclic one having generally 1 to 40 carbon atoms, preferably 1 to 20 carbon atoms, more preferably 1 to 10 carbon atoms and furthermore preferably 1 to 6 carbon atoms, which is specifically exemplified by, for example, straight chained or branched groups such as a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a n-heptyl group, an isoheptyl group, a sec-heptyl group, a tert-heptyl group, a n-octyl group, a sec-octyl group, a tert-octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group, an icosyl group, a docosyl group, a tetracosyl group, apentacosyl group, aheptacosyl group, a triacontyl group, a dotriacontyl group, a hexacontyl group and an octacontyl group; saturated aliphatic monocyclic groups such as a cyclopropyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group, a cyclooctadecyl group, a cyclononadecyl group and a cycloicosyl group; unsaturated aliphatic monocyclic groups such as a cyclobutenyl group, a cyclopentenyl group, a cyclohexenyl group, a cycloheptenyl group, a cyclooctenyl group and a cyclononenyl group; saturated or unsaturated aliphatic polycyclic groups such as a tricyclodecyl group, a dicyclopentadienyl group, a perhydronaphthyl group, a perhydroanthryl group, a norbornyl group, a norpinyl group, a norcaranyl group and an adamantyl group.

The aryl group represented by $R^{10}$ includes one having generally 6 to 14 carbon atoms and preferably 6 to 10 carbon atoms, which is specifically exemplified by, for example, a phenyl group, a naphthyl group and an anthryl group.

The aralkyl group represented by $R^{10}$ includes one having generally 7 to 10 carbon atoms, which is specifically exemplified by, for example, a benzyl group, a phenylethyl group, a phenylpropyl group and a phenylbutyl group.

The above-described alkyl group, aryl group and aralkyl group represented by $R^{10}$ may contain generally 1 to 10 hetero atoms, preferably 1 to 3 hetero atoms and more preferably one hetero atom. These hetero atoms include, for example, oxygen atom, sulfur atom and nitrogen atom, which are present in the group in a form of a group such as —NH—, —O—, —S—, —NHR— (wherein R represents an alkyl group, an aryl group or an aralkyl group) —N=, —C(=O)—NH—, —S(=O)—NH—, —C(=O)— and —S(=O)—.

Here, an alkyl group, an aryl group and an aralkyl group represented by R of the group shown by —NHR— include the similar one to an alkyl group, an aryl group and an aralkyl group represented by $R^4$ of the above-described general formula [2].

Further, the alkyl group represented by $R^{10}$ may have generally 1 to 10 substituents, preferably 1 to 5 substituents and more preferably 1 to 3 substituents. These substituents include, for example, alkoxy groups having 1 to 6 carbon atoms such as a methoxy group, an ethoxy group, a propyloxy group, a butoxy group, a pentyloxy group and a hexyloxy group; halogen atoms such as chlorine atom, bromine atom, fluorine atom and iodine atom; a hydroxyl group; and an amino group.

The aryl group and the aralkyl group represented by $R^{10}$ may have generally 1 to 10 substituents, preferably 1 to 5 substituents and more preferably 1 to 3 substituents. These substituents include, for example, straight chained branched or cyclic alkyl group having 1 to 6 carbon atoms such as a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a cyclopropyl group, a cyclobutyl group, a cyclopentyl group and a cyclohexyl group; alkoxy groups having 1 to 6 carbon atoms such as a methoxy group, an ethoxy group, a propyloxy group, a butoxy group, a pentyloxy group and a hexyloxy group; halogen atoms such as chlorine atom, bromine atom, fluorine atom and iodine atom; a hydroxyl group; and an amino group.

In the above-described nitro compound represented by the general formula [6], $R^{10}$ is preferably an aryl group. Among others, nitrobenzene derivatives such as nitrobenzene, nitrotoluene and nitroxylene are preferable, and nitrobenzene is particularly preferable.

The hydrogen source in the method of the present invention includes, for example, gases such as hydrogen, carbon monoxide and ethylene; alcohols such as methanol, ethanol, isopropyl alcohol and butanol; hydrazines such as hydrazine, methylhydrazine, ethylhydrazine, tert-butylhydrazine, allylhydrazine and phenylhydrazine or salts thereof (for example, hydrochloride, sulfate, acetate and oxalate thereof); carboxylic acids such as formic acid and acetic acid; or salts thereof (for example, alkali metal salts such as sodium salt and potassium salt); hypophosphites such as sodium hypophosphite and potassium hypophosphite; ammonium formate; decaline; and formaldehyde. Among others, hydrazines are preferable, and hydrazine is particularly preferable. As the above-described hydrazines, hydrates thereof and hydrazines containing water in advance can also be used.

Amount of the hydrogen source to be used is generally 1 to 100 times by mole and preferably 1 to 50 times by mole to the nitro compound which is a reaction substrate in the method of the present invention. When hydrazine is used as a hydrogen source, an amount of hydrazine to be used is generally 1 to 100 times by mole, preferably 1 to 50 times by mole, and more preferably 1 to 10 times by mole to the nitro compound.

When hydrazines are used as a hydrogen source, said hydrazines may be used as they are in the method of the present invention, but preferably they may be used after dissolving in water so that concentrations of said hydrazines become generally 10 to 100% by weight and preferably 50 to 100% by weight.

Amount of the platinum catalyst fixed on an ion-exchange resin to be used is such one that an amount of the platinum fixed becomes generally $1.0 \times 10^{-6}$ to 1 times by mole and preferably $1.0 \times 10^{-4}$ to 0.4 times by mole to the nitro compound which is a substrate.

In the method of the present invention, it may be possible that further addition of a poisoning agent (generally designated as a catalytic poison substance) against the catalytic action of the platinum catalyst fixed on an ion-exchange resin to the reaction system further improve selectivity of hydroxylamine.

The poisoning agent includes, for example, sulfur-containing compounds such as dimethyl sulfoxide and diethyl sulfoxide; heavy metal ions such as a mercury ion, an arsenic ion, a lead ion, a bismuth ion and an antimony ion; halides such as sodium iodide and potassium iodide; amines such as trimethylamine, triethylamine, pyridine and morpholine; phosphines such as triphenylphosphine, diphenyl(tert-butyl) phosphinomethane, diphenyl(tert-butyl) phosphinoethane and diphenyl(tert-butyl)phosphinopropane; carbon monoxide; and carbon dioxide. Among others, sulfur-containing compounds are preferable, and dimethyl sulfoxide is particularly preferable.

Amount of the poisoning agent to be used is generally 0 to 100% by weight, preferably 0 to 30% by weight, and more preferably 0 to 10% by weight.

When the nitro compound, the hydrogen source and the like to be used in the method of the present invention are liquid, further use of a reaction solvent may not be required because these substances play a role of solvent.

The reaction solvent includes, for example, water and an organic solvent such as alcohols such as methanol, ethanol, n-propanol, isopropanol, n-butanol, isobutanol, sec-butanol and tert-butanol; ketones such as acetone and methyl ethyl ketone; nitrites such as acetonitrile and butyronitrile; halogenated hydrocarbons such as dichloromethane, 1,2-dichloroethane, chloroform and carbon tetrachloride; ethers such as diethyl ether, dimethoxyethane, diethoxyethane and tetrahydrofuran; hydrocarbons such as n-hexane, n-heptane and cyclohexane; aromatic hydrocarbons such as benzene, toluene and xylene; esters such as ethyl acetate and butyl acetate. These solvents may be used alone or in a proper combination of 2 or more types. Further, selectivity of the reaction can be varied by a reaction solvent or a combination thereof to be used.

When water and an organic solvent are used in combination, ratio of water to the organic solvent is generally 0.0001 to 100 times by weight, preferably 0.001 to 100 times by weight, more preferably 0.01 to 50 times by weight, and further more preferably 0.01 to 20 times by weight.

Amount of the reaction solvent to be used is generally 1 to 50 times by weight, preferably 1 to 20 times by weight, and more preferably 1 to 10 times by weight to the nitro compound which is a reaction substrate.

In the method of the present invention, any reaction method of batch, semi-batch and continuous methods of suspension bed system or flow on fixed bed system may be used so long as surface of the platinum catalyst fixed on an ion-exchange resin in the reaction vessel is contacted with liquid of raw material and the like.

Reaction temperature is generally −20 to 200° C., preferably 10 to 100° C., and more preferably 10 to 70° C.

Reaction time is generally 1 minute to 24 hours, preferably 10 minutes to 16 hours, and more preferably 30 minutes to 12 hours.

Reaction pressure is generally atmospheric pressure to 10 MPa and preferably atmospheric pressure to 2 MPa.

Thus, hydroxylamine compound can be obtained, for example, by mixing a nitro compound as a substrate with about 1 to 50 times by weight of a solvent to said nitro compound, adding thereto a platinum catalyst fixed on an anion-exchange resin so that platinum present in the catalyst becomes $1 \times 10^{-6}$ to 1 times by mole, and further adding hydrazine in an amount of 1 to 100 times by mole to the nitro compound as a substrate and a poisoning agent in an amount of 0 to 100% by weight to the nitro compound as a substrate, followed by reacting under reflux for about 1 minute to 24 hours with stirring, after completion of the reaction, removing the platinum catalyst fixed on an anion-exchange resin by filtering, concentrating the reaction liquid, and purifying if necessary.

By the above-described method of the present invention, a nitro group of the nitro compound represented by the above general formula [6] is converted to a hydroxyamono group to give a corresponding hydroxylamine compound represented by the general formula [7]:

$$R^{10}\text{---NHOH} \qquad [7]$$

(wherein, $R^{10}$ represents the same as the above)

In the method of the present invention, the hydroxyamino group of the objective hydroxylamine compound represented by the general formula [7] is sometimes reduced to an amino group as similarly seen in the conventional method. However, since formation ratio of the byproduct is extremely lower compared to the conventional method, the objective hydroxylamine compound can be obtained in very high yield. Further, as described above, the platinum catalyst fixed on an ion-exchange resin which was used in the reaction can be isolated from the reaction liquid after the reaction and repeatedly reused as a catalyst for various reactions without losing activity thereof. Still further, since particle size of the platinum catalyst fixed on an ion-exchange resin of the present invention is very large, handling of said catalyst in recovery and reuse thereof is very easy.

Herein below, the present invention will be explained in more detail using Examples, but the present invention is not limited thereto by any means.

EXAMPLES

Example 1

Synthesis of a Platinum Catalyst Fixed on an Anion-Exchange Resin of the Present Invention To 62.5 mL of 1N hydrochloric acid solution containing $9.6 \times 10^{-3}$ M of $K_2PtCl_4$, 15 g of an anion-exchange resin made of styrene/divinylbenzene copolymer having a group represented by the following formula:

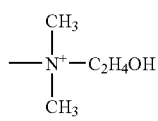

as an ion-exchange group (Trade Name: IRA-410JC1, made by Organo Corp.) was added at room temperature under stirring, and the reaction liquid was subjected to a reaction for 10 minutes at the same temperature under stirring. After completion of the reaction, the resin was washed with methanol and water in this order. Further, 50 mL of water and 0.2 mL of hydrazine were added thereto at room temperature, followed by reacting for 1 hour under stirring. After completion of the reaction, the resin was washed with methanol and water in this order, then vacuum dried to obtain 15.2 g of black colored platinum catalyst fixed on an ion-exchange resin. The amount of platinum supported in the platinum catalyst fixed on an ion-exchange resin obtained was about 1% by weight from the result of measurement by weight change.

Example 2

Synthesis of a Platinum Catalyst Fixed on an Anion-Exchange Resin of the Present Invention To 62.5 mL of 1N hydrochloric acid solution containing $9.6 \times 10^{-3}$ M of $K_2PtCl_4$, 15 g of an anion-exchange resin made of styrene/divinylbenzene copolymer having a group represented by the following formula:

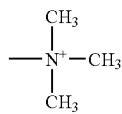

as an ion-exchange group (Trade Name: IRA-400JC1, made by Organo Corp.) was added at room temperature under stirring, and the reaction liquid was subjected to a reaction for 10 minutes at the same temperature under stirring. After completion of the reaction, the resin was washed with methanol and water in this order. Further, 50 mL of water and 0.2 mL of hydrazine were added thereto at room temperature, followed by reacting for 1 hour under stirring. After completion of the reaction, the resin was washed with methanol and water in this order, then vacuum dried to obtain 15.2 g of black colored platinum catalyst fixed on an ion-exchange resin. The amount of platinum supported in the platinum catalyst fixed on an ion-exchange resin obtained was about 1% by weight from the result of measurement by weight change.

Example 3

Synthesis of a Platinum Catalyst Fixed on a Cation-Exchange Resin of the Present Invention To 62.5 mL of an aqueous solution containing $9.6 \times 10^{-3}$ M of $[(H_2NCH_2CH_2NH_2Pt](NO_3)_2$, 15 g of a regenerated cation-exchange resin made of styrene/divinylbenzene copolymer having a sulfonic acid group as an ion-exchange group (Trade Name: IR-120B Na, made by Organo Corp.) was added at room temperature under stirring, and the reaction liquid was subjected to a reaction for 10 minutes at the same temperature under stirring. After completion of the reaction, the resin was washed with methanol and water in this order. Further, 50 mL of water and 0.2 mL of hydrazine were added thereto at room temperature, followed by reacting for 1 hour under stirring. After completion of the reaction, the resin was washed with methanol and water in this order, then vacuum dried to obtain 15.2 g of black colored platinum catalyst fixed on an ion-exchange resin. The amount of platinum supported in the platinum catalyst fixed on an ion-exchange resin obtained was about 1% by weight to the whole catalyst from the result of measurement by weight change.

Example 4

Synthesis of a Platinum Catalyst Fixed on a Cation-Exchange Resin of the Present Invention To 62.5 mL of an aqueous solution containing $9.6 \times 10^{-3}$ M of $[(H_2NCH_2CH_2NH_2) Pt]Cl_2$, 15 g of a regenerated cation-exchange resin made of styrene/divinylbenzene copolymer having a sulfonic acid group as an ion-exchange group (Trade Name: IR120B Na, made by Organo Corp.) was added at room temperature with stirring, and the reaction liquid was subjected to a reaction for 10 minutes at the same temperature under stirring. After completion of the reaction, the resin was washed with methanol and water in this order. Further, 50 mL of water and 0.2 mL of hydrazine were added thereto at room temperature, followed by reacting for 1 hour under stirring. After completion of the reaction, the resin was washed with methanol and water in this order, then vacuum dried to obtain 15.2 g of black colored platinum catalyst fixed on an ion-exchange resin. The amount of platinum supported in the platinum catalyst fixed on an ion-exchange resin obtained was about 1% by weight to the whole catalyst from the result of measurement by weight change.

Example 5

Synthesis of a Hydroxylamine Compound of the Present Invention

Into a reaction vessel, 10 mL of nitrobenzene (98 mmol), 100 mL of isopropyl alcohol, 0.05 mL of dimethylsulfoxide and 4 g of the platinum catalyst fixed on an ion-exchange resin obtained in Example 1 were charged, and 20 mL of hydrazine was added thereto dropwise over 1 hour, followed by reacting the reaction liquid under reflux for 4 hours under stirring. After completion of the reaction, the platinum catalyst fixed on an ion-exchange resin in the reaction liquid was removed by filtration, and the solution obtained was concentrated followed by recrystallization in isopropyl alcohol to obtain 10 g of phenylhydroxylamine (yield 95%).

The obtained compound was confirmed to be phenylhydroxylamine by the $^1$H-NMR spectrum measurement.

Example 6

Synthesis of a Hydroxylamine Compound of the Present Invention

Into a reaction vessel, 10 mL of nitrobenzene (98 mmol), 100 mL of methanol, 0.05 mL of dimethylsulfoxide and 4 g of the platinum catalyst fixed on an ion-exchange resin obtained in Example 1 were charged, and 20 mL of hydrazine was added thereto dropwise over 1 hour, followed by reacting the reaction liquid under reflux for 4 hours under stirring. After completion of the reaction, the platinum catalyst fixed on an ion-exchange resin in the reaction liquid was removed by filtration, and the solution obtained was concentrated followed by recrystallization in methanol to obtain 9.7 g of phenylhydroxylamine (yield 92%).

The obtained compound was confirmed to be phenylhydroxylamine by the $^1$H-NMR spectrum measurement.

Example 7

After the same reaction procedures as in Example 6 proceeded, the platinum catalyst fixed on an ion-exchange resin was removed from the reaction liquid by filtration, and volume of the mother liquid was adjusted exactly to 100 mL, which was analyzed by a high performance liquid chromatography to obtain, by calculation remaining ratio of nitrobenzene as a raw material, yield of the obtained phenylhydroxylamine and formation ratio of aniline as a byproduct. The platinum catalyst fixed on an ion-exchange resin filtered out was repeatedly used for the same reaction several times after washing with methanol. The reaction liquid after completion of each reaction was analyzed by a high performance liquid chromatography in the same manner as described above to obtain ratios of responding in each reaction (remaining ratio of nitrobenzene, yield of phenylhydroxylamine and formation ratio of aniline). Results are shown in Table 1.

TABLE 1

| Number of repeated use of | Ratio of responding (%) | | |
|---|---|---|---|
| the catalyst | Nitrobenzene | Phenylhydroxylamine | Aniline |
| 1 | 0.5 | 97.2 | 2.2 |
| 2 | 0.9 | 96.1 | 3.0 |
| 3 | 1.1 | 97.9 | 1.0 |
| 4 | 2.2 | 96.3 | 1.5 |
| 5 | 1.6 | 96.1 | 2.2 |
| 6 | 0.7 | 97.7 | 1.6 |
| 7 | 0.7 | 97.2 | 2.1 |

As clear from Table 1, it was proved that even if the platinum catalyst fixed on an ion-exchange resin of the present invention was used repeatedly for the reaction, yield of the objective phenylhydroxylamine did not decrease and formation ratio of the byproduct was also maintained at low level. From the results, it is understood that the platinum catalyst fixed on an ion-exchange resin of the present invention is hardly deactivated by the repeated use.

INDUSTRIAL APPLICABILITY

According to the method of the present invention where a platinum catalyst fixed on a matrix of an ion-exchange resin is used, the objective hydroxylamine compound can be manufactured efficiently, more industrially and safely with little formation of a byproduct. Further, the platinum catalyst fixed on an ion-exchange resin of the present invention is hardly deactivated even if repeatedly used many times because platinum metal is fixed on a matrix of the ion-exchange resin, and handling in recovery, reuse and the like of said catalyst is extremely easy because particle size of said catalyst is very large.

What is claimed is:

1. A method for producing a hydroxylamine compound, comprising:
   contacting a nitro compound with a hydrogen source in the presence of a platinum catalyst fixed on an ion-exchange resin,
   wherein the hydrogen source is hydrazine and the platinum catalyst fixed on an ion-exchange resin is obtained by adsorbing a platinum-containing ion in an aqueous solvent derived from a platinum compound with the ion-exchange resin followed by subjecting the ion to a reductive treatment, and
   the platinum compound is selected from the group consisting of ammonium hexachloroplatinate, ammonium tetrachloroplatinate, potassium hexachloroplatinate, potassium tetrachloroplatinate, potassium tetrabromoplatinate, sodium hexachloroplatinate, sodium tetrachloroplatinate, platinum nitrate, platinum sulfate, platinum acetate, and platinum complexes coordinated with a ligand selected from the group consisting of 1,5-cyclooctadiene (COD), dibenzylideneacetone (DBA), norbornadiene (NBD), tricyclohexylphosphine (PCγ$_3$), triethoxyphosphine (P(OEt)$_3$, tri-tert-butylphosphine (P(O'Bu)$_3$, bipyridine (BPY), phenanthroline (PHE), triphenylphosphine (PPh$_3$), 1,2-bis(diphenylphosphino)ethane (DPPE), triphenoxyphosphine (P(OPh)$_3$), trimethoxyphosphine (P(OCH$_3$)$_3$), ethylene (CH$_2$=CH$_2$), amine(NH$_3$), N$_2$ and PO$_3$.

2. The method according to claim 1, wherein the nitro compound is a nitrobenzene derivative.

3. The method according to claim 1, wherein a nitro compound is further contacted with a poisoning agent.

4. The method according to claim 3, wherein the poisoning agent is dimethylsulfoxide.

5. The method according to claim 1, wherein an ion-exchange resin used in preparation of the platinum catalyst fixed on an ion-exchange resin is a polystyrene copolymer cross-linked with divinylbenzene which has an ion-exchange group bonded to an aromatic ring thereof.

6. The method according to claim 1, wherein an ion-exchange resin used in the preparation of the platinum catalyst fixed on an ion-exchange resin is a polyacrylic ester which has an ion-exchange group bonded to a carbonyl moiety of an ester group thereof.

7. The method according to claim 5 or 6, wherein the ion-exchange group is an anion-exchange group.

8. The method according to claim 7, wherein the anion-exchange group is selected from the group consisting of a primary amino group, a secondary amino group, a tertiary amino group, a quaternary ammonium group and an alkyldiamine group.

9. The method according to claim 8, wherein the tertiary amino group is selected from the group consisting of a dimethylamino group, a methylethylamino group and a diethylamino group, and the quaternary ammonium group is selected from the group consisting of the following groups:

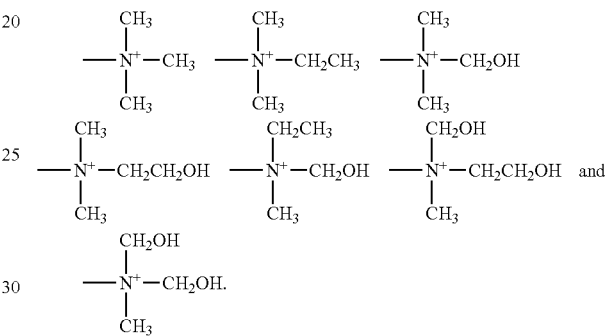

10. The method according to claim 5 or 6, wherein the ion-exchange group is a cation-exchange group.

11. The method according to claim 10, wherein the cation-exchange group is selected from the group consisting of a sulfonic acid group, a carboxyl group and a phenolic hydroxyl group.

12. The method according to claim 3, wherein amount of the poisoning agent is 1 to 30% by weight to the nitro compound.

13. The method according to claim 1, wherein the platinum compound is potassium tetrachloroplatinate or sodium tetrachloroplatinate.

14. The method according to claim 1, wherein yield of hydroxylamine is 90% and over.

* * * * *